(12) United States Patent
Robinson et al.

(10) Patent No.: US 10,095,112 B2
(45) Date of Patent: *Oct. 9, 2018

(54) MULTIPLE TRIGGER PHOTORESIST COMPOSITIONS AND METHODS

(71) Applicants: Alex Phillip Graham Robinson, Birmingham (GB); Alexandra McClelland, Worcestershire (GB); Andreas Frommhold, Dera (DE); Dongxu Yang, Sichuan (CN); John Roth, Cohasset, MA (US)

(72) Inventors: Alex Phillip Graham Robinson, Birmingham (GB); Alexandra McClelland, Worcestershire (GB); Andreas Frommhold, Dera (DE); Dongxu Yang, Sichuan (CN); John Roth, Cohasset, MA (US)

(73) Assignee: IRRESISTIBLE MATERIALS LTD, Birmingham (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/441,919

(22) Filed: Feb. 24, 2017

(65) Prior Publication Data

US 2018/0246408 A1    Aug. 30, 2018

(51) Int. Cl.
*G03F 7/004*        (2006.01)
*G03F 7/038*        (2006.01)
(Continued)

(52) U.S. Cl.
CPC ......... *G03F 7/0382* (2013.01); *C08G 83/008* (2013.01); *G03F 7/0045* (2013.01);
(Continued)

(58) Field of Classification Search
CPC ...... G03F 7/038; G03F 7/0382; G03F 7/2004; G03F 7/38; G03F 7/40; C07C 2604/00; C08G 83/008; H01L 21/0274
(Continued)

(56) References Cited

U.S. PATENT DOCUMENTS 8,034,546 B2 * 10/2011  Robinson .............. G03F 7/0382
                                                     430/270.1
8,758,979 B2 *  6/2014  Robinson .............. B82Y 30/00
                                                     430/270.1
(Continued)

*Primary Examiner* — Amanda C. Walke
(74) *Attorney, Agent, or Firm* — James G. Shelnut; Charles R Szmanda; The Patent Practice of Szmanda & Shelnut LLC

(57) ABSTRACT

The present disclosure relates to novel multiple trigger negative working photoresist compositions and processes. The processes involve removing acid-labile protecting groups from crosslinking functionalities in a first step and crosslinking the crosslinking functionality with an acid sensitive crosslinker in a second step. The incorporation of a multiple trigger pathway in the resist catalytic chain increases the chemical gradient in areas receiving a low dose of irradiation, effectively acting as a built in dose depend quencher-analog and thus enhancing chemical gradient and thus resolution, resolution blur and exposure latitude. The photoresist compositions and the methods are ideal for fine pattern processing using, for example, ultraviolet radiation, beyond extreme ultraviolet radiation, extreme ultraviolet radiation, X-rays and charged particle rays.

18 Claims, 5 Drawing Sheets

SEM images of (a) PHOST 1 and (b) PBOCST 1 resist patterns after 30 keV electron beam exposure.

(51) Int. Cl.
*G03F 7/16* (2006.01)
*G03F 7/20* (2006.01)
*G03F 7/38* (2006.01)
*G03F 7/32* (2006.01)
*C08G 83/00* (2006.01)
*H01L 21/027* (2006.01)

(52) U.S. Cl.
CPC ............ *G03F 7/0046* (2013.01); *G03F 7/162* (2013.01); *G03F 7/168* (2013.01); *G03F 7/2004* (2013.01); *G03F 7/2037* (2013.01); *G03F 7/325* (2013.01); *G03F 7/38* (2013.01); *H01L 21/0274* (2013.01); *C07C 2604/00* (2017.05)

(58) Field of Classification Search
USPC ............ 430/270.1, 322, 325, 329, 330, 331; 558/275
See application file for complete search history.

(56) References Cited

U.S. PATENT DOCUMENTS 9,323,149 B2 * 4/2016 Robinson .............. G03F 7/0384
9,383,646 B2 * 7/2016 Robinson .............. G03F 7/0384

* cited by examiner

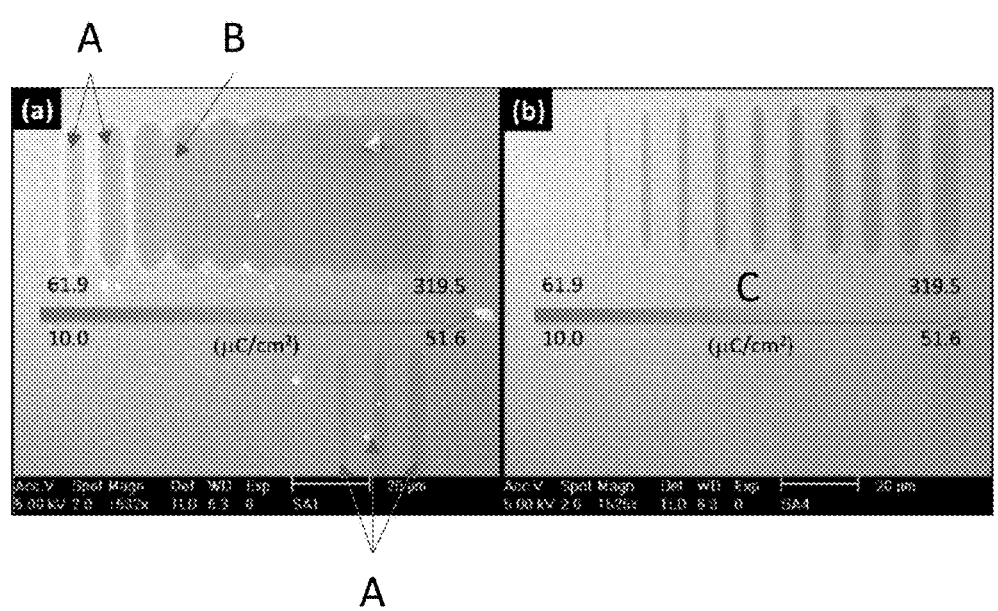
Figure 1. SEM images of (a) PHOST 1 and (b) PBOCST 1 resist patterns after 30 keV electron beam exposure.

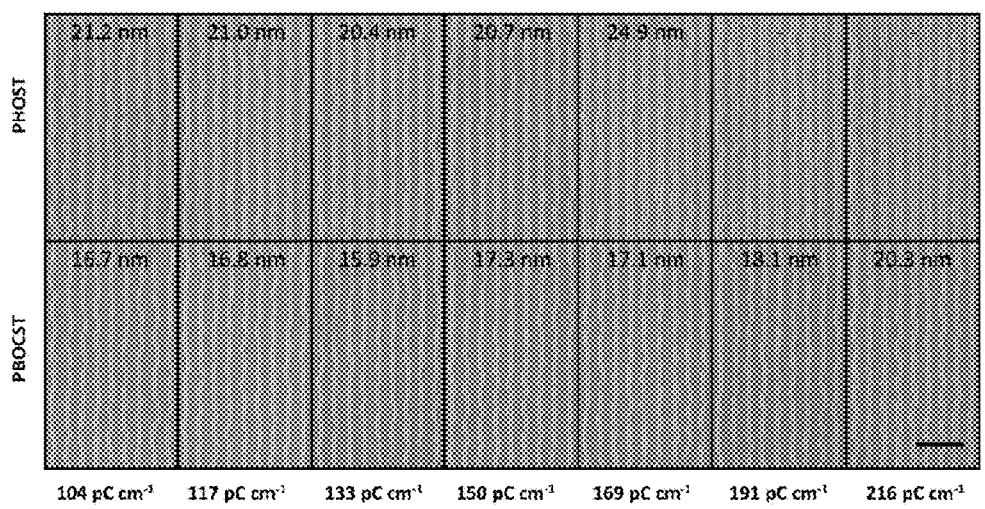
Figure 2. SEM images of electron beam exposed 60 nm pitch lines in PHOST 2 (top) and PBOCST 2 (bottom) resists with various doses. 30 keV electron beam was used for patterning. The critical dimension (CD) values are shown in the individual images. Scale bar: 200 nm.

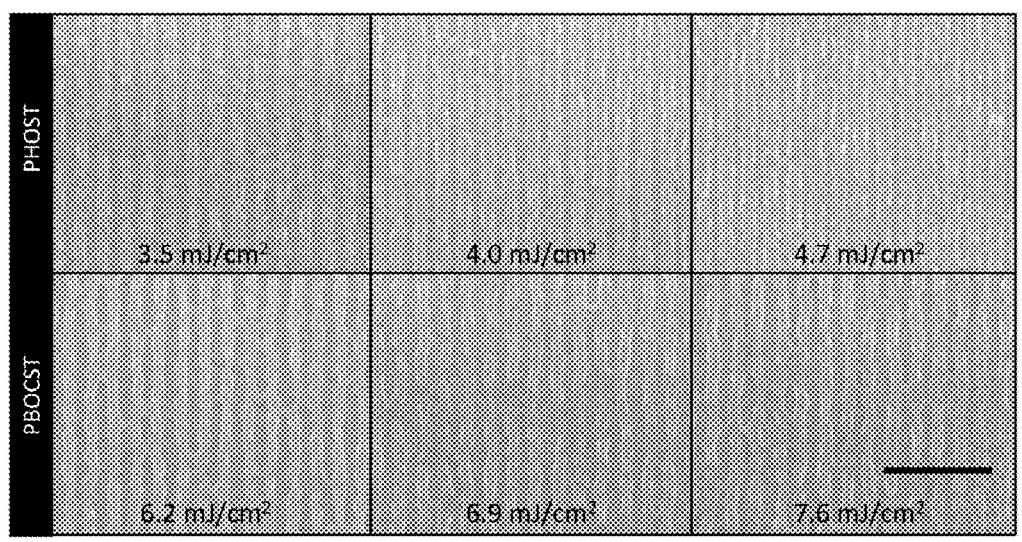
Figure 3. SEM images of EUV exposed 44 nm pitch lines patterned in PHOST 2 (top) and PBOCST 2 (bottom) resists with various doses. The dose-to-wafer details are shown in the individual images. Scale bar: 200 nm.

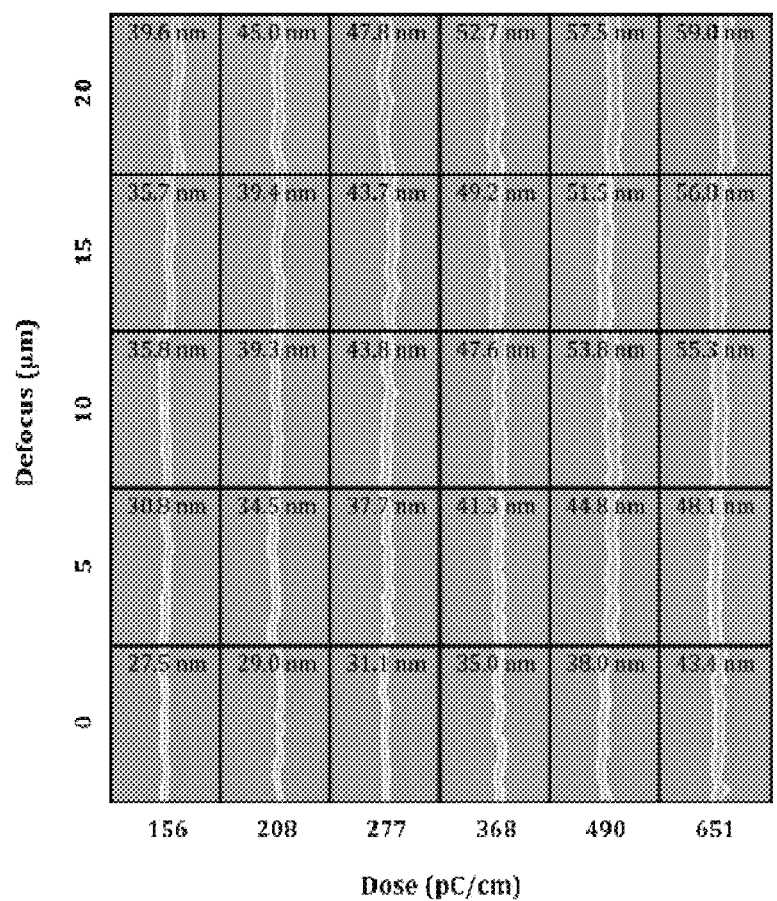
Figure 4. The matrix of SEM images with various doses and defocus level for the PHS 2 resist. The critical dimension (CD) values are shown in the individual images.

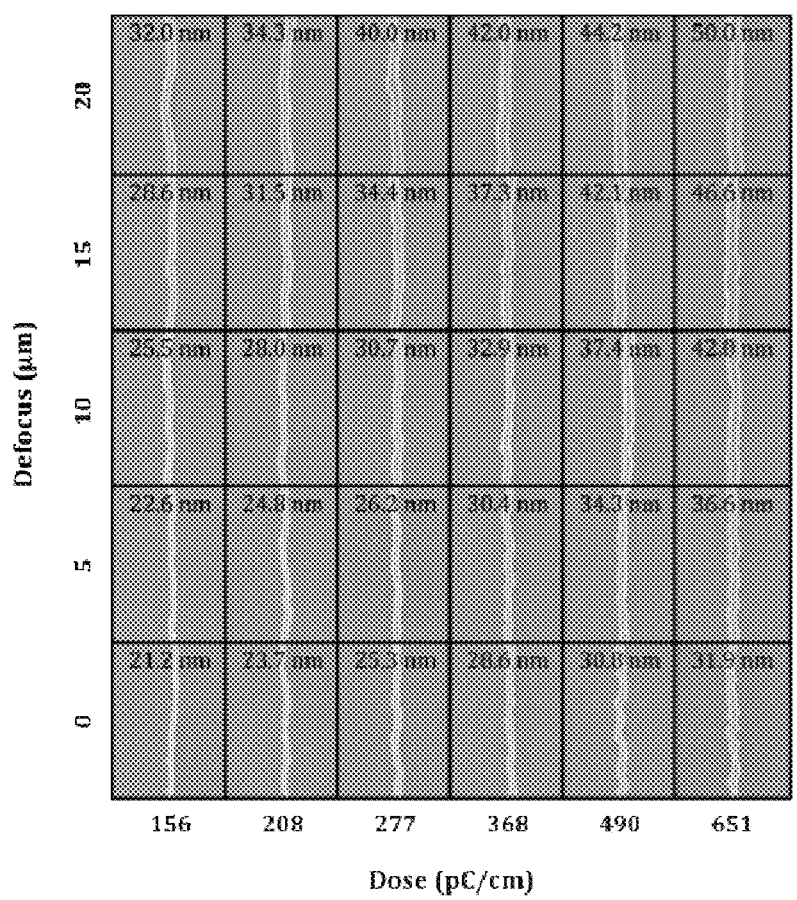
Figure 5. The matrix of SEM images with various doses and defocus level for the PBOCST 2 resist. The critical dimension (CD) values are shown in the individual images.

MULTIPLE TRIGGER PHOTORESIST COMPOSITIONS AND METHODS

FIELD OF INVENTION

The present invention relates to novel negative-type photoresist compositions and methods of using them. The invention further relates to multiple trigger photoresist processes which allow for improvement in contrast, resolution, and/or line edge roughness in some systems without giving up sensitivity. The photoresist compositions and the methods of the current disclosure are ideal for fine pattern processing using, for example, ultraviolet radiation, extreme ultraviolet radiation, beyond extreme ultraviolet radiation, X-rays and charged particle rays exposure.

BACKGROUND

As is well known in the industry, the manufacturing process of various kinds of electronic or semiconductor devices such as ICs, LSIs and the like involves a fine patterning of a resist layer on the surface of a substrate material such as a semiconductor silicon wafer. This fine patterning process has traditionally been conducted by the photolithographic method in which the substrate surface is uniformly coated with a positive or negative tone photoresist composition to form a thin layer of the photoresist composition and selectively irradiating with actinic rays (such as ultraviolet light) through a photomask followed by a development treatment to selectively dissolve away the photoresist layer in the areas exposed or unexposed, respectively, to the actinic rays leaving a patterned resist layer on the substrate surface. The thus obtained patterned resist layer is utilized as a mask in the subsequent treatment on the substrate surface such as etching, plating, chemical vapor deposition and the like. The fabrication of structures with dimensions of the order of nanometers is an area of considerable interest since it enables the realization of electronic and optical devices which exploit novel phenomena such as quantum confinement effects and allows greater component packing density. Thus, the resist layer is required to have an ever-increasing fineness. One method which can be used to accomplish this is by using actinic rays having a shorter wavelength than the conventional ultraviolet light, such as, for example, electron beams (e-beams), excimer laser beams, EUV, BEUV and X-rays, used as the short wavelength actinic rays. Needless to say, the minimum size obtainable is primarily determined by the performance of the resist material and the wavelength of the actinic rays. Various materials have been proposed as suitable resist materials.

Many positive photoresists they generally apply a technique called "chemical amplification" to the polymeric resist materials. A chemically amplified resist material is generally a multi-component formulation in which there is a main polymeric component, such as a novolac resin which contributes towards properties such as resistance of the material to etching, mechanical stability and developability; and one or more additional components which impart desired properties to the resist and a photoacid generator. Typically, a portion of the hydroxy groups of a phenolic polymer, such as a novolac, a polyhydroxystyrene and the like, is protected by a functional group which reacts with an acid and is removed to de-protect the hydroxy group making the hydroxy group available for other reactions, which in positive photoresists is developability. By definition, the chemical amplification occurs through a catalytic process involving the sensitizer which results in a single irradiation event causing a cascading effect by reacting with multiple functional groups of the protected novolac molecules. In a typical example the resist comprises a polymer and a photoacid generator (PAG) as sensitizer. The PAG releases a proton in the presence of actinic radiation (light or e-beam). This proton then reacts with the polymer to cause it to lose the functional group thus deprotecting the hydroxy group. In the process, a second proton is generated which can then react with a further molecule.

Many negative photoresists rely on photogenerated acid to cause either crosslinking or polymerization of the resist components so that the exposed areas are insoluble to developers, either solvent or aqueous based, particularly aqueous base developers. The process for these resists generally require a heating step to efficiently and effectively cause the reactions, polymerization or crosslinking, to occur since at room temperature there is not enough polymerization or crosslinking to make the resist impervious to the developer. Most of these negative working resists also require a post bake to further cure the remaining resist patterns.

Negative photoresists have also been described which combine chemically amplified positive resist chemistry with negative working curing agents, such as crosslinkers. In these photoresists, a phenolic polymer, whose hydroxy groups are partially protected, is combined with a crosslinker and a photoacid generator. During exposure, the protected hydroxy groups are de-protected and free to react with the crosslinking groups, see for example, U.S. Pat. No. 6,114,082 to Hakey. In this disclosure, the phenolic polymer is required to be partially protected (75% protection) so that, after exposure, an aqueous base developer can solubilize the unexposed areas thus allowing a negative image to remain. Also disclosure is the requirement that post exposure heating be performed to properly cure the resist to prevent the developer from attacking the exposed areas of the resist. The speed of the curing reaction can be controlled, for example, by heating the resist film after exposure (post exposure bake or PEB) to drive the reaction that causes the loss of the functional group and/or the crosslinking/curing. Also during heating, the reacted polymer molecules are free to react with remaining components of the formulation, as would be suitable for a negative-tone resist. As mentioned these systems require heating of the resist to complete the required crosslinking so that the exposed areas are insoluble to the developer.

A well-known and documented issue with chemically amplified resists is a phenomenon knowns as "resist blur" or "dark reaction". In the process the photogenerated acid migrates away from the exposed areas (acid migration) and into the unexposed areas where it can cause unwanted reactions. In positive resists, line sharpening results and in negative resists line-broadening results. Various methods and resist components have been introduced to control acid diffusion such as the addition of base quenchers which react with diffused acid to remove it from the system prior to any unwanted resist reactions. Addition of base quencher itself bring limitation such as reduced sensitivity, developer issues, etc. Additionally, since most resists require PEB the increased temperature impart higher kinetic energy to the system and thus the acid resulting in increased levels of migration and thus line broadening. In some cases, where small critical dimensions (CD) are required, the exposure latitude of these systems is severely reduced including line bridging and poor resolution.

As can be seen there is an ongoing desire to obtain finer and finer resolution of photoresists that will allow for the manufacture of smaller and smaller semiconductor devices in order to meet the requirements of current and further needs. In order to achieve these lofty goals line broadening and line edge roughness need to be reduced, as well as exposure latitude and contrast need to be improved. It is thus desirable to create materials, compositions and methods which can be used in conjunction with these photoresist processes to create these improvements.

DESCRIPTION OF THE FIGURES

FIG. 1: shows SEM images of (a) PHOST 1 and (b) PBOCST 1 resist patterns after 30 keV electron beam exposure.

FIG. 2: shows SEM images of electron beam exposed 60 nm pitch lines in PHOST 2 (top) and PBOCST 2 (bottom) resists with various doses. 30 keV electron beam was used for patterning. The critical dimension (CD) values are shown in the individual images. Scale bar: 200 nm.

FIG. 3: shows SEM images of EUV exposed 44 nm pitch lines patterned in PHOST 2 (top) and PBOCST 2 (bottom) resists with various doses. The dose-to-wafer details are shown in the individual images. Scale bar: 200 nm.

FIG. 4: shows the matrix of SEM images with various doses and defocus level for the PHS 2 resist. The critical dimension (CD) values are shown in the individual images.

FIG. 5: shows the matrix of SEM images with various doses and defocus level for the PBOCST 2 resist. The critical dimension (CD) values are shown in the individual images.

SUMMARY OF THE DISCLOSURE

In a first embodiment, a multiple trigger negative-working photoresist composition is disclosed comprising a) at least one polymer, oligomer or monomer, each comprising two or more crosslinkable functionalities, wherein essentially all the functionalities are attached to acid labile protecting groups, b) at least one acid activated crosslinker, and c) at least one photoacid generator.

In a second embodiment, the multiple trigger photoresist composition of the above embodiment is disclosed, wherein at least about 90% of the crosslinkable functionalities are attached to acid labile protecting group.

In a third embodiment, a multiple trigger photoresist composition of the above embodiments is disclosed, wherein the acid-labile protecting group is capable of being removed when exposed to acid under ambient conditions providing a functionality capable of crosslinking with the crosslinking system when the crosslinking system is catalyzed by acid.

In a fourth embodiment, a multiple trigger photoresist composition of the above embodiments is disclosed, wherein the acid labile protecting group comprises a tertiary alkoxycarbonyl group.

In a fifth embodiment, a multiple trigger photoresist composition of the above embodiments is disclosed, wherein the at least one photoacid generator comprises an onium salt compound, a triphenylsulphonium salt, a sulfonimide, a halogen-containing compound, a sulfone, a sulfonate ester, a quinone-diazide, a diazomethane, an iodonium salt, an oxime sulfonate, or a dicarboxyimidyl sulfate.

In a sixth embodiment, a multiple trigger photoresist composition of the above embodiments is disclosed, wherein the at least one acid activated crosslinker comprises an acid catalyzed monomer, oligomer or polymer, and may be at least one of a glycidyl ether, glycidyl ester, an oxetane, a glycidyl amine, a methoxymethyl group, an ethoxy methyl group, a butoxymethyl group, a benzyloxymethyl group, dimethylamino methyl group, diethylamino methyl amino group, a dialkylolmethyl amino group, a dibutoxymethyl amino group, a dimethylolmethyl amino group, diethylolmethyl amino group, a dibutylol methyl amino group, a morpholino methyl group, acetoxymethyl group, benzyloxy methyl group, formyl group, acetyl group, vinylgroup or an isopropenyl group. or one or more glycidyl ether groups attached to an aryl monomer, oligomer or polymer.

In a seventh embodiment, a multiple trigger photoresist composition of the above embodiments is disclosed, which is photoimageable by at least one of UV, deep UV, extreme UV, x-ray, or e-beam actinic radiation.

In an eighth embodiment, a multiple trigger photoresist composition of the above embodiments is disclosed, wherein the photoresist is capable of being developed in solvent, aqueous base or combinations thereof.

In a ninth embodiment, a method of forming a patterned resist layer on a substrate comprising the steps of: providing a substrate, applying the photoresist composition of any of the above embodiments to a desired wet thickness, heating the coated substrate to form a substantially dried coating to obtain a desired thickness, imagewise exposing the coated substrate to actinic radiation, and removing the unexposed areas of the coating using an aqueous, solvent or a combination aqueous-solvent developer composition; wherein the remaining photoimage pattern is optionally heated.

DETAILED DESCRIPTION

As used herein, the conjunction "and" is intended to be inclusive and the conjunction "or" is not intended to be exclusive unless otherwise indicated. For example, the phrase "or, alternatively" is intended to be exclusive.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

As used herein the phrase "acid labile protecting group" refers to a group which has the property of reacting with an acid to result in its removal and thus deprotecting a functionality to which it was bound.

As used herein, the terms "dry", "dried" and "dried coating" means having less than 8% residual solvent.

As used herein the phrase "essentially all" means at least 90%.

The current disclosure describes a multiple trigger negative-working photoresist composition is disclosed comprising a) at least one polymer, oligomer or monomer, each comprising two or more crosslinkable functionalities, wherein essentially all the functionalities are attached to acid labile protecting groups, b) at least one acid activated crosslinker, and c) at least one photoacid generator. It has surprisingly been found that when essentially all the crosslinkable functionalities of a polymer, oligomer or monomer are attached to acid labile protecting groups in combination with acid activated crosslinkers, a major improvement in resolution, resolution blur, exposure latitude with tunable sensitivity when processed, via what is believed to be a multiple trigger negative working resist process as will be described below.

The crosslinkable functionalities used in negative working photoresists are well known in the industry and include, for example, hydroxy, amino, oximes, and the like. The functionalities in the presence of acid and an acid activated crosslinker will react to crosslink. These functional groups are attached to a ballast group such as an aryl group, which may be a substituted or unsubstituted divalent aromatic group, such aromatic groups include, for example the phenylenes (—$C_6H_4$—), the fused divalent aromatic group, such as, for example, the naphthylenes (—$C_{10}H_6$—), the anthracenylenes (—$C_{14}H_8$—) and the like, as well as the heteroaromatic groups, such as, for example, the nitrogen heterocycles: pyridines, quinolines, pyrroles, indoles, pyrazoles, the triazines, and other nitrogen-containing aromatic heterocycles well known in the arts, as well as the oxygen heterocycles: furans, oxazoles and other oxygen-containing aromatic heterocycles, as well the sulfur containing aromatic heterocycles, such as, for example, thiophenes. Trivalent and tetravalent aromatics can also be used.

The aryl groups may be in the form of an oligomer or a polymer with a molecular weight between about 1000 daltons and 100,000 daltons and higher depending on the desired properties of the cured negative resist pattern, such as etch resistance. Examples include the novolac resins based on phenol, the cresols, the resorcinols, the pyrogallols and the like which also include co-polymers made therefrom. Also, polyhydroxystyrene based polymers and their derivatives or co-polymers may be used in these photoresist compositions.

The crosslinkable functionalities are blocked, or protected, by acid labile protecting groups. Acid labile protecting group, including, for example, substituted methyl groups, 1-substituted ethyl groups, 1-substituted alkyl groups, silyl groups, germyl groups, alkoxycarbonyl group, acyl groups and cyclic acid-dissociable groups. The substituted methyl groups include, for example, the methoxymethyl group, methylthiomethyl group, ethoxy methyl group, ethylthiomethyl group, methoxyethoxy methyl group, benzyloxymethyl group, benzylthiomethyl group, phenacyl group, bromophenacyl group, methoxyphenacyl group, methylthiophenacyl group, α-methylphenacyl group, cyclopropylmethyl group, benzyl group, diphenyl methyl group, triphenylmethyl group, bromobenzyl group, nitrobenzyl group, methoxybenzyl group, methylthiobenzyl group, ethoxy benzyl group, ethylthiobenzyl group, piperonyl group, methoxycarbonylmethyl group, ethoxy carbonylmethyl group, N-propoxy carbonylmethyl group, isopropoxy carbonylmethyl group, N-butoxycarbonylmethyl group and t-butoxycarbonylmethyl group. The 1-substituted ethyl groups include, for example. 1-methoxyethyl group, 1-methylthioethyl group, 1,1-dimethoxyethyl group, 1-ethoxy ethyl group, 1-ethylthioethyl group, 1,1-diethoxy ethyl group, 1-phenoxyethyl group, 1-phenylthioethyl group, 1,1-diphenoxyethyl group, 1-benzyloxyethyl group, 1-benzylthioethyl group, 1-cyclopropylethyl group, 1-phenylethyl group, 1,1-diphenyl ethyl group, 1-methoxycarbonylethyl group, 1-ethoxy carbonylethyl group, 1-N-propoxy carbonylethyl group, 1-isopropoxy carbonylethyl group, 1-N-butoxycarbonylethyl group and the 1-t-butoxycarbonylethyl group. The 1-substituted alkyl group include the isopropyl group, sec-butyl group, t-butyl group, 1,1-dimethylpropyl group, 1-methylbutyl group and 1,1-dimethylbutyl group.

The acid labile protecting groups may contain silyl functionalities and include, for example, the trimethyl silyl group, ethyldimethylsilyl group, methyldiethylsilyl group, triethylsilyl group, isopropyldimethylsilyl group, methyldiisopropylsilyl group, triisopropylsilyl group, t-butyldimethylsilyl group, methyldi-t-butylsilyl group, tri-t-butylsilyl group, phenyldimethylsilyl group, methyldiphenyl silyl group and triphenylsilyl group. The germyl groups include, for example, the trimethyl germyl group, ethyldimethylgermyl group, methyldiethylgermyl group, triethylgermyl group, isopropyldimethylgermyl group, methyldiisopropylgermyl group, triisopropylgermyl group, t-butyldimethylgermyl group, methyldi-t-butylgermyl group, tri-t-butylgermyl group, phenyldimethylgermyl group, methyldiphenyl germyl group and triphenylgermyl group.

Other acid labile protecting groups include alkoxycarbonyl acid labile protecting groups including, for example, the methoxycarbonyl group, ethoxy carbonyl group, isopropoxy carbonyl group and t-butoxycarbonyl group. Acyl acid labile protecting groups may be used and include, for example, the acetyl group, propionyl group, butyryl group, heptanoyl group, hexanoyl group, valeryl group, pivaloyl group, isovaleryl group, lauroyl group, myristoyl group, palmitoyl group, stearoyl group, oxaryl group, malonyl group, succinyl group, glutaryl group, adipoyl group, piperoyl group, suberoyl group, azelaoyl group, sebacoyl group, acrylyl group, propioloyl group, methacryloyl group, crotonoyl group, oleoyl group, maleoyl group, fumaroyl group, mesaconoyl group, camphoroyl group, benzoyl group, phthaloyl group, isophthaloyl group, terephthaloyl group, naphthoyl group, toluoyl group, hydroatropoyl group, atropoyl group, cinnamoyl group, furoyl group, thenoyl group, nicotinoyl group, isonicotinoyl group, p-toluene sulfonyl group and the mesyl group.

Additional acid labile protecting groups include cyclic acid labile protecting groups and include, for example, the cyclopropyl group, cyclopentyl group, cyclohexyl group, cyclohexanyl group, 4-methoxycyclohexyl group, tetrahydropyranyl group, tetrahydrofuranyl group, tetrahydrothiopyranyl group, tetrahydrothiofuranyl group, 3-bromo tetrahydropyranyl group, 4-methoxy tetrahydropyranyl group, 4-methoxy tetrahydrothiopyranyl group and 3-tetrahydrothiophene-1,1-dioxy group.

Acid activated crosslinkers suitable for the current disclosure constitute compounds able to crosslink with the crosslinkable functionalities mentioned above during the process such that when deprotected to provide for example, a phenol or similar group, the crosslinker will react with the now deprotected —OH group situated on the phenol or similar group. The crosslinkers may be a polymer, an oligomer or a monomer. Not to be held to theory, it is believed that the acid that is generated by exposure to the actinic radiation not only reacts with the acid-labile protecting group of the polymer, oligomer or monomer, as the first trigger, but aids in the reaction of the crosslinker with the crosslinkable functionality as the second trigger to cause a curing reaction. Such curing reaction decreases the developer solubility of the exposed and now reacted areas to result in a pattern of cured material. Examples of crosslinkers include compounds comprising at least one type of substituted group that possess a cross-linking reactivity with a hydroxy group, such as from a phenol, an amine or similar group of the polymer, oligomer, or monomer. Specific examples of the acid activated crosslinker include the glycidyl ether group, glycidyl ester group, glycidyl amino group, methoxymethyl group, ethoxy methyl group, benzyloxymethyl group, dimethylamino methyl group, diethylamino methyl group, dimethylol amino methyl group, diethylol amino methyl group, morpholino methyl group, acetoxymethyl group, benzyloxy methyl group, formyl group, acetyl group, vinyl group and isopropenyl group.

Examples of compounds having the aforementioned acid activated crosslinker include, for example, bisphenol A-based epoxy compounds, bisphenol F-based epoxy compounds, bisphenol S-based epoxy compounds, novolac resin-based epoxy compound, resole resin-based epoxy compounds, and poly (hydroxystyrene)-based epoxy compounds.

Acid activated crosslinkers based on melamines are useful for the current disclosure and include, for example methylol group-containing melamine compounds, methylol group-containing benzoguanamine compounds, methylol group-containing urea compounds, methylol group-containing phenol compounds, alkoxyalkyl group-containing melamine compounds, alkoxyalkyl group-containing benzoguanamine compounds, alkoxyalkyl group-containing urea compounds, alkoxyalkyl group-containing phenol compounds, carboxymethyl group-containing melamine resins, carboxymethyl group-containing benzoguanamine resins, carboxymethyl group-containing urea resins, carboxymethyl group-containing phenol resins, carboxymethyl group-containing melamine compounds, carboxymethyl group-containing benzoguanamine compounds, carboxymethyl group-containing urea compounds, and carboxymethyl group-containing phenol compounds, methylol group-containing phenol compounds, methoxymethyl group-containing melamine compounds, methoxymethyl group-containing phenol compounds, methoxymethyl group-containing glycol-uril compounds, methoxymethyl group-containing urea compounds and acetoxymethyl group-containing phenol compounds. The methoxymethyl group-containing melamine compounds are commercially available as, for example, CYMEL300, CYMEL301, CYMEL303, CYMEL305 (manufactured by Mitsui Cyanamid), the methoxymethyl group-containing glycol-uril compounds are commercially available as, for example, CYMEL117 4 (manufactured by Mitsui Cyanamid), and the methoxymethyl group-containing urea compounds are commercially available as, for example, MX290 (manufactured by Sanwa Chemicals).

Other acid activated crosslinkers include epoxy crosslinkers. Illustrative of the epoxies employed within the scope of the present invention include polymeric, oligomeric, and monomeric aliphatic and aromatic epoxies, including, for example, cycloaliphatic epoxies, bisphenol A epoxies, 3,4-epoxycyclohexyl methyl 3,4-epoxy cyclohexyl carboxylate, and the like. Also included are epoxy formulations based on glycidyl ethers of para amino phenols as described in U.S. Pat. No. 5,514,729. Other suitable epoxies that may be employed to practice the present invention include, but are not limited to, those derived from bisphenol S, bisphenol F, novolak resins, and the epoxies obtained from the reaction of bisphenol A and epihalohydrins. Such epoxies are described in U.S. Pat. No. 5,623,031. Other suitable epoxies that may be employed to practice the present invention are disclosed in U.S. Pat. Nos. 5,602,193; 5,741,835; and 5,910,548. Further examples of epoxies useful for the current disclosure are the glycidyl ethers and glycidyl esters of novolac based polymers, oligomers, and monomers, and the oxetanes.

The photo acid generators (PAGs) suitable for the multiple trigger negative working photoresist of the current disclosure include onium salt compounds, sulfone imide compounds, halogen-containing compounds, sulfone compounds, ester sulfonate compounds, quinonediazide compounds, and diazomethane compounds. Specific examples of these acid generators are indicated below.

Examples of onium salt compounds include sulfonium salts, iodonium salts, phosphonium salts, diazonium salts and pyridinium salts. Specific examples of onium salt compounds include diphenyl(4-phenylthiophenyl)sulphonium hexafluoroantimonate, 4,4'-bis[diphenylsulfonylphenylsulphide bis hexafluoroantimonate and combinations there of, triphenylsulfonium nonafluorobutanesulfonate, triphenylsulfonium trifluoromethanesulfonate, triphenylsulfonium pyrenesulfonate, triphenylsulfonium dodecylbenzenesulfonate, triphenylsulfonium p-toluene sulfonate, triphenylsulfonium benzenesulfonate, triphenylsulfonium 10-camphor-sulfonate, triphenylsulfonium octanesulfonate, triphenylsulfonium 2-trifluoromethyl benzenesulfonate, triphenylsulfonium hexafluoroantimonate, triarylsulfonium hexafluoroantimonates, the triarylsulfonium hexafluorophosphates, the triarylsulfonium tetrafluoroborates as well as other tetrafluoroborates, triphenylsulfonium napthalenesulfonate, tri(4-hydroxyphenyl)sulfonium nonafluorobutanesulfonate, tri(4-hydroxyphenyl) sulfoniumtrifluoromethanesulfonate, tri(4-hydroxyphenyl)sulfonium pyrenesulfonate, tri(4-hydroxyphenyl) sulfoniumdodecylbenzenesulfonate, tri(4-hydroxyphenyl)sulfonium p-toluene sulfonate, tri(4-hydroxyphenyl)sulfonium benzenesulfonate, tri(4-hydroxyphenyl)sulfonium 10-camphor-sulfonate, tri (4-hydroxyphenyl)sulfonium octanesulfonate, tri(4-hydroxyphenyl)sulfonium 2-trifluoromethylbenzenesulfonate, tri(4-hydroxyphenyl)sulfonium hexafluoroantimonate, tri(4-hydroxyphenyl)sulfonium napthalenesulfonate, diphenyliodonium nonafluorobutanesulfonate, diphenyliodonium trifluoromethanesulfonate, diphenyliodonium pyrenesulfonate, diphenyliodonium dodecylbenzenesulfonate, diphenyliodonium p-toluene sulfonate, diphenyliodonium benzenesulfonate, diphenyliodonium 10-camphor-sulfonate, diphenyliodonium octanesulfonate, diphenyliodonium 2-trifluoromethylbenzenesulfonate, bis(4-t-butylphenyl)iodonium nonafluorobutanesulfonate, bis(4-t-butylphenyl)iodonium trifluoromethanesulfonate, bis(4-t-butylphenyl) iodonium pyrenesulfonate, bis(4-t-butylphenyl)iodonium dodecylbenzenesulfonate, bis(4-t-butylphenyl)iodonium p-toluene sulfonate, bis(4-t-butylphenyl)iodonium benzenesulfonate, bis(4-t-butylphenyl)iodonium 10-camphor-sulfonate, bis(4-t-butylphenyl)iodonium octanesulfonate, bis(4-t-butylphenyl)iodonium 2-trifluoromethylbenzenesulfonate, 4-hydroxy-1-naphthyl tetrahydrothiophenium trifluoromethanesulfonate and 4,7-dihydroxy-1-naphthyl tetrahydrothiophenium trifluoromethanesulfonate.

Specific examples of a sulfone imide compound include N-(trifluoromethylsulfonyloxy)succinimide, N-(trifluoromethylsulfonyloxy)phthalimide, N-(trifluoromethylsulfonyloxy)diphenylmaleimide, N-(trifluoromethylsulfonyloxy)bicyclo[2.2.1]hepto-5-ene-2,3-dicarboxyimide, N-(trifluoromethylsulfonyloxy)-7-oxabicyclo[2.2.1]hepto-5-ene-2,3-dicarboxyimide, N-(trifluoromethylsulfonyloxy) bicyclo[2.2.1]heptane-5,6-oxy-2,3-dicarboxyimide, N-(trifluoromethylsulfonyloxy)naphthylimide, N-(10-camphor-sulfonyloxy)succinimide, N-(10-camphor-sulfonyloxy) phthalimide, N-(10-camphor-sulfonyloxy)diphenyl maleimide, N-(10-camphor-sulfonyloxy)bicyclo[2.2.1] hepto-5-ene-2,3-dicarboxyimide, N-(10-camphor-sulfonyloxy)-7-oxabicyclo[2.2.1]hepto-5-ene-2,3-dicarboxyimide, N-(10-camphor-sulfonyloxy)bicyclo[2.2.1]heptane-5,6-oxy-2,3-dicarboxyimide, N-(10-camphor-sulfonyloxy) naphthylimide, N-(p-toluene sulfonyloxy)succinimide, N-(p-toluene sulfonyloxy)phthalimide, N-(p-toluene sulfonyloxy)diphenyl maleimide, N-(p-toluene sulfonyloxy)bicyclo[2.2.1]hepto-5-ene-2,3-dicarboxyimide, N-(p-toluene sulfonyloxy)-7-oxabicyclo[2.2.1]hepto-5-ene-2,3-dicarboxyimide, N-(p-toluene sulfonyloxy) bicyclo[2.2.1]heptane-5,6-oxy-2,3-dicarboxyimide, N-(p-toluene sulfonyloxy)naphthylimide, N-(2-trifluoromethylbenzenesulfonyloxy)succinimide, N-(2-trifluoromethylbenzenesulfonyloxy)phthalimide, N-(2-trifluoromethylbenzenesulfonyloxy)diphenyl maleimide, N-(2-trifluoromethylbenzenesulfonyloxy)bicyclo[2.2.1]hepto-5-ene-2,3-dicarboxyimide, N-(2-trifluoromethylbenzenesulfonyloxy)-7-oxabicyclo[2.2.1]hepto-5-ene-2,3-dicarboxyimide, N-(2-trifluoromethylbenzenesulfonyloxy) bicyclo[2.2.1]heptane-5,6-oxy-2,3-dicarboxyimide, N-(2-trifluoromethylbenzenesulfonyloxy) naphthylimide, N-(4-fluorobenzenesulfonyloxy)succinimide, N-(4-fluorobenzenesulfonyloxy)phthalimide, N-(4-fluorobenzenesulfonyloxy)diphenyl maleimide, N-(4-fluorobenzenesulfonyloxy)bicyclo[2.2.1]hepto-5-ene-2,3-dicarboxyimide, N-(4-fluorobenzenesulfonyloxy)-7-oxabicyclo[2.2.1]hepto-5-ene-2,3-dicarboxyimide, N-(4-fluorobenzenesulfonyloxy) bicyclo[2.2.1]heptane-5,6-oxy-2,3-dicarboxyimide, N-(4-fluorobenzenesulfonyloxy) naphthylimide, N-(nonafluorobutylsulfonyloxy)succinimide, N-(nonafluorobutylsulfonyloxy)phthalimide, N-(nonafluorobutylsulfonyloxy)diphenyl maleimide, N-(nonafluorobutylsulfonyloxy)bicyclo[2.2.1]hepto-5-ene-2,3-dicarboxyimide, N-(nonafluorobutylsulfonyloxy)-7-oxabicyclo[2.2.1]hepto-5-ene-2,3-dicarboxyimide, N-(nonafluorobutylsulfonyloxy) bicyclo[2.2.1]heptane-5,6-oxy-2,3-dicarboxyimide and N-(nonafluorobutylsulfonyloxy) naphthylimide.

Examples of halogen-containing compounds include, for example, haloalkyl group-containing hydrocarbon compounds and haloalkyl group-containing heterocyclic compounds. Specific examples of halogen-containing compounds include (poly)trichloromethyl-s-triadine derivatives such as phenyl-bis(trichloromethyl)-s-triadine, 4-methoxyphenyl-bis(trichloromethyl)-s-triadine and 1-naphthyl-bis(trichloromethyl)-s-triadine, and 1,1-bis(4-chlorophenyl)-2,2,2-trichloroethane.

Examples of sulfone compounds include, for example, β-ketosulfone and β-sulfonylsulfone, and the α-diazo compounds thereof. Specific examples of the sulfone compounds include phenacyl phenylsulfone, mesitylphenacyl sulfone, bis(phenylsulfonyl)methane, 1,1-bis(phenylsulfonyl) cyclobutane, 1,1-bis(phenylsulfonyl) cyclopentane, 1,1-bis(phenylsulfonyl) cyclo hexane, and 4-trisphenacyl sulfone.

Examples of sulfonate ester compounds include alkylsulfonate esters, haloalkyl sulfonate esters, aryl sulfonate esters sand imino sulfonates. Specific examples of sulfonate ester compounds include benzoin tosylate, pyrogallol tristrifluoromethanesulfonate, pyrogallol trisnonafluorobutanesulfonate, pyrogallol methanesulfonate triester, nitrobenzyl-9,10-diethoxy anthracene-2-sulfonate, α-methylol benzoin tosylate, α-methylol benzoin octanesulfonate, α-methylol benzoin trifluoromethanesulfonate and α-methylol benzoin dodecylsulfonate.

Examples of quinine diazide compounds include compounds containing a 1,2-quinone diazide sulfonyl group such as the 1,2-benzoquinone diazide-4-sulfonyl group, 1,2-naphthoquinone diazide-4-sulfonyl group, 1,2-naphtho quinine diazide-5-sulfonyl group and 1,2-naphthoquinone diazide-6-sulfonyl group. Specific examples of quinone diazide compounds include 1,2-quinone diazidesulfonate esters of (poly) hydroxyphenylaryl ketones such as 2,3,4-trihydroxybenzophenone, 2,4,6-trihydroxybenzophenone, 2,3,4,4'-tetrahydroxybenzophenone, 2,2',3,4-tetrahydroxybenzophenone, 3'-methoxy-2,3,4,4'-tetrahydroxybenzophenone, 2,2', 4,4'-tetrahydroxybenzophenone, 2,2'3,4,4'-pentahydroxybenzophenone, 2,2'3,4,6'-pentahydroxybenzophenone, 2,3,3'4,4',5'-hexahydroxybenzophenone, 2,3'4,4',5',6-hexahydroxybenzophenone; 1,2-quinone diazide sulfonate esters of bis[(poly) hydroxyphenyl]alkanes such as bis(4-hydroxyphenyl) methane, bis(2,4-dihydroxyphenyl) methane, bis(2,3,4-trihydroxyphenyl) methane, 2,2-bis(4-hydroxyphenyl) propane, 2,2-bis(2,4-dihydroxyphenyl) propane and 2,2-bis(2,3,4-trihydroxyphenyl) propane; 1,2-quinone diazide sulfonate esters of (poly) hydroxytriphenylalkanes such as 4,4'-dihydroxytriphenylmethane, 4,4',4"-trihydroxytriphenylmethane, 2,2',5,5'-tetramethyl-2",4,4'-trihydroxytriphenylmethane, 3,3',5,5'-tetramethyl-2",4,4'-trihydroxytriphenylmethane, 4,4',5,5'-tetramethyl-2,2',2"-trihydroxytriphenylmethane, 2,2',5,5'-tetramethyl-4,4',4"-trihydroxytriphenylmethane, 1,1,1-tris (4-hydroxyphenyl) ethane, 1,1-bis(4-hydroxyphenyl)-1-phenylethane, 1,1-bis(4-hydroxyphenyl)-1-[4-{1-(4-hydroxyphenyl)-1-methylethyl}phenyl]ethane, 1,1,3-tris (2,5-dimethyl-4-hydroxyphenyl) propane, 1,1,3-tris (2,5-dimethyl-4-hydroxyphenyl) butane and 1,3,3-tris (2,5-dimethyl-4-hydroxyphenyl) butane; and 1,2-quinone diazide sulfonate esters of (poly) hydroxyphenylflavans such as 2,4,4-trimethyl-2',4',7-trihydroxy-2-phenylflavan and 2,4,4-trimethyl-2',4',5',6',7-pentahydroxy-2-phenylflavan.

Specific examples of diazomethane compounds include bis(trifluoromethylsulfonyl)diazomethane, bis(cyclohexylsulfonyl)diazomethane, bis(phenylsulfonyl) diazomethane, bis(p-toluene sulfonyl) diazomethane, methylsulfonyl-p-toluene sulfonyldiazomethane, 1-cyclohexylsulfonyl-1-(1,1-dimethylethylsulfonyl)diazomethane and bis(1,1-dimethylethylsulfonyl)diazomethane.

The compositions of the current disclosure may contain one or more of the above mentioned photoacid generators.

Examples of suitable solvents for the current disclosure include ethers, esters, etheresters, ketones and ketoneesters and, more specifically, ethylene glycol monoalkyl ethers, diethylene glycol dialkyl ethers, propylene glycol monoalkyl ethers, propylene glycol dialkyl ethers, acetate esters, hydroxyacetate esters, lactate esters, ethylene glycol monoalkylether acetates, propylene glycol monoalkylether acetates, alkoxyacetate esters, (non-)cyclic ketones, acetoacetate esters, pyruvate esters and propionate esters. Specific examples of these solvents include ethylene glycol monomethyl ether, ethylene glycol monoethyl ether, ethylene glycol monopropyl ether, ethylene glycol monobutyl ether, diethylene glycol dimethyl ether, diethylene glycol diethyl ether, diethylene glycol dipropyl ether, diethylene glycol dibutyl ether, methylcellosolve acetate, ethyl cellosolve acetate, propylene glycol monomethyletheracetate, propylene glycol monoethyletheracetate, propylene glycol monopropyletheracetate, isopropenyl acetate, isopropenyl propionate, methylethyl ketone, cyclohexanone, 2-heptanone, 3-heptanone, 4-heptanone, 2-hydroxypropionate ethyl, 2-hydroxy-2-methylpropionate ethyl, ethoxy acetate ethyl, hydroxyacetate ethyl, 2-hydroxy-3-methyl methylbutyrate, 3-methoxybutylacetate, 3-methyl-3-methoxybutylacetate, 3-methyl-3-methoxybutyl propionate, 3-methyl-3-methoxybutyl butylate, ethyl acetate, propyl acetate, butyl acetate, methyl acetoacetate, ethyl acetoacetate, methyl 3-methoxypropionate, ethyl 3-methoxy propionate, 3-ethoxy propionate methyl and 3-ethoxy propionate ethyl. The aforementioned solvents may be used independently or as a mixture of two or more types. Furthermore, at least one type of high boiling point solvent such as benzylethyl ether, dihexyl ether, diethylene glycol monomethyl ether, diethylene glycol monoethyl ether, acetonylacetone, isoholon, caproic acid, capric acid, 1-octanol, 1-nonanol, benzyl alcohol, benzyl acetate, ethyl benzoate, diethyl oxalate, diethyl maleate, γ-butyrolactone, ethylene carbonate, propylene carbonate and phenylcellosolve acetate may be added to the aforementioned solvent.

Various additives may be added to the photoresist formulations to provide certain desirable characteristic of the photoresist such as, for example, acid diffusion control agents to retard acid from migrating into unexposed areas of the coating, surfactants to improve coating of substrates, adhesion promoters to improve adhesion of the coating to the substrate and sensitizers to improve the photosensitivity of the photoresist coating during photoexposure, and anti-foaming agents and air release agents, as well as other materials well know in the coatings industry.

The crosslinkable functionalities are all blocked by the acid labile protecting groups from about 90% to about 100% blocked. The acid labile groups have the well-known property of having the capability of being removed when exposed to acid and optionally heat.

The components of the compositions of the current disclosure are included in ranges as follows based on weight/weight: the protected polymer, oligomer or monomer from about 1% to about 65%, acid activated crosslinker from about 10% to about 80%, photoacid generator from about 0.5% to about 50%. The percent solids of the composition may range from about 0.001%-about 25%.

The photoresist compositions can be coated onto substrate such as a silicon wafer or a wafer coated with silicon dioxide, aluminum, aluminum oxide, copper, nickel, any of a number of semiconductor materials or nitrides or other substrates well known the semiconductor industry, or a substrate having thereon an organic film, such as, for example, a bottom layer anti-reflective film or the like. The photoresist compositions are applied by such processes as spin coating, curtain coating, slot coating, dip coating, roller coating, blade coating and the like. After coating, the solvent is removed to a level wherein the coating can be properly exposed. In some cases a residual of 5% solvent may remain in the coating while in other cases less than 1% is required. Drying can be accomplished by hot plate heating, convection heating, infrared heating and the like. The coating is imagewise exposed through a mark containing a desired pattern.

Radiation suitable for the described photoresist compositions include, for example, ultraviolet rays (UV), such as the bright line spectrum of a mercury lamp (254 nm), a KrF excimer laser (248 nm), and an ArF excimer laser (193 nm), extreme ultraviolet (EUV) such as 13.5 nm from plasma discharge and synchrotron light sources, beyond extreme ultraviolet (BEUV) such as 6.7 nm exposure, X-ray such as synchrotron radiation. Ion beam lithography and charged particle rays such as electron beams may also be used.

Following exposure, the exposed coated substrate may optionally be post exposure baked to enhance the reaction of the photoacid generator, such as, for example, heating from about 30 to about 200° C. for about 10 to about 600 seconds. This may be accomplished by hot plate heating, convection heating, infrared heating and the like. The heating may also be performed by a laser heating processes such as, for example, a $CO_2$ laser pulse heating for about 2 to about 5 milliseconds. Both heating processes may be combined in tandem.

A flood exposure process may optionally be applied after the pattern exposure to aid in further cure. Results have indicated that flood exposure reduces or eliminates pattern collapse after development of the negative-tone resists as well as reduction in line edge roughness. For example, a 532 nm continuous wave laser exposes the previously exposed resist for 1-2 sec followed by wet development. The flood process may or may not be followed by a heating step.

The unexposed areas are next moved using a developer. Such developers generally include organic solvents. The develop solvent is less aggressive than the solvent that was used in preparing the photoresist composition.

After development a final baking step may be included to further enhance the curing of the now exposed and developed pattern. The heating process may be, for example, from about 30 to about 300° C. for about 10 to about 120 seconds and may be accomplished by hot plate heating, convection heating, infrared heating and the like.

Not to be held to theory, it is believed that the curing of the system involves multiple triggers, in the example below, a 2-step process wherein the protected crosslinking functionality and the crosslinker must both be exposed to an acid in order for them to react. When the PAG is exposed to actinic radiation, acid is produced which will deprotect the crosslinking functionality which is now available for crosslinking with the crosslinker only when radiation produced acid activates the crosslinker in the presence of the crosslinking functionality. Because two reactions are required it is believed that "acid migration" or "dark reaction" is quelled and resist blur is reduced and resolution and exposure latitude are significantly improved. See Scheme 1 below. In theory if a third reaction were required to cure the negative working photoresist, a further improvement in resolution blur, resolution and exposure latitude would occur.

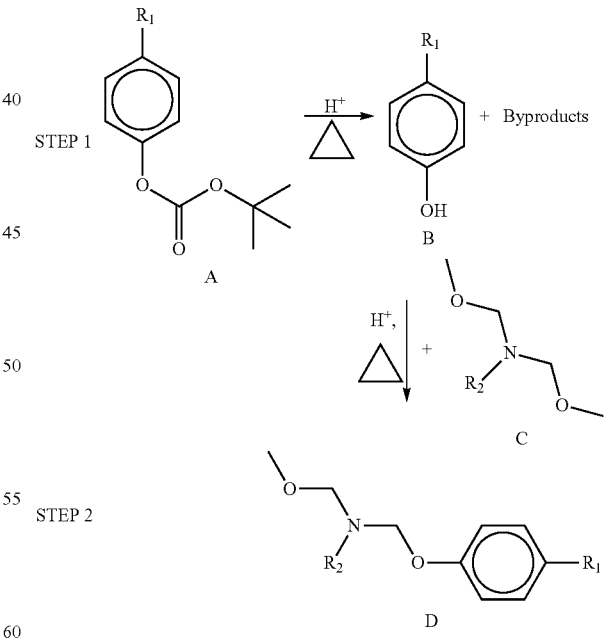

Scheme 1

In Scheme 1 the protected crosslinkable functionality A is deprotected when in the presence of acid $H^+$, and results in the deprotected compound B, where the functionality is —OH. The crosslinker C, in the presence of an acid, and the crosslinkable functionality can now react together to give the cured material D.

Examples below and the following discussion will demonstrate the surprising improvement of the current disclosure.

EXAMPLES

As used in the examples HMMM is hexamethoxymethylmelamine (Sigma Aldrich), PHOST is polyhydroxystyrene (MW=approx. 2500) synthesized at University of Warwick, PBOCST is poly(4-t-butyloxycarbonyloxystyrene) (MW=approx. 2500) synthesized at University of Warwick, PGEF is poly((phenylglycidylether)-co-formaldehyde) (Huntsman Chemical) and PAG is triphenylsulphonium hexafluoroantimonate (Midori Kagaku).

PHOST 1: Into a 100 mL of propylene glycol monomethyl ether (PGME) was added 0.50 g of HMMM acid activated crosslinker, 0.50 g of PHOST and 0.25 g of PAG and stirred for 1 hr at room temp.

PHOST 2: Into a 100 mL of propylene glycol monomethyl ether (PGME) was added 0.50 g of PGEF acid activated crosslinker, 0.25 g of PHOST and 0.25 g of PAG and stirred for 1 hr at room temp.

PBOCST 1: PHOST 1 was repeated substituting PHOST with PBOCST.

PBOCST 2: PHOST 2 was repeated substituting HMMM with PGEF.

Silicon chips diced from a 100 mm wafer (Rockwood Electronic Materials, n-type, <100>) were used as substrates for all of the process examples. The substrates were cleaned with a 10 min sonication in acetone followed by 10 min in isopropyl alcohol (IPA). By adjusting the spin speed, a 30-40 nm resist film was prepared for sensitivity tests while a ~30 nm film was spun for high-resolution tests. A post-application bake (PAB) was applied after spin coating. The PAB conditions were 70° C./1 min for HMMM crosslinker and 70° C./5 min for CL12-01 crosslinker, respectively.

Lithographic Evaluation

An FEI XL30 SFEG field emission scanning electron microscope with ELPHY Plus pattern generator (Raith GmbH) was used for e-beam exposures. For sensitivity and contrast evaluation, a set of 50×50 μm squares with electron doses ranging from 0.5 μC/cm$^2$ to 1000 μC/cm$^2$ were patterned using a 20 keV electron beam. The remaining film thickness of each square after development was measured using a surface profiler (Dektak 3st Auto). A sigmoid function was used to fit the response curve to extract the sensitivity (i.e. dose for the 50% remaining film thickness). For high-resolution electron beam evaluations, a 30 keV acceleration voltage was used with ~20 pA beam current. When single pixel lines were used, the dosage was described as line dose (pC/cm). EUV exposures with a 13.5 nm wavelength were performed using the interference lithography set-up of the XIL beamline. Various post-exposure bake (PEB) conditions were used in this study. The developer was a mixture of monochlorobenzene (MCB) and IPA [1:1]. A dip development for 20 s followed by a rinse in IPA for several seconds was applied. Where possible the SEM images of resist patterns were analyzed with the software package SUMMIT to extract the critical dimension (CD) values.

HMMM Acid Activated Crosslinker
Sensitivity Evaluation

The comparative sensitivity of PHOST 1 and PBOCST 1 was evaluated. Various PEB temperatures were applied from no PEB (room temperature of 20° C.) to 140° C. PEB. The sensitivity values from fitting are shown in Table 1. For PHOST 1, exposed patterns started showing up from 90° C. PEB with sensitivity of 51.6 μC/cm$^2$. Considerable improvement of resist sensitivity was obtained by increasing the PEB temperature to above 120° C. A layer of residual film was observed at the un-exposed area at 140° C. PEB, possibly due to thermal crosslinking. On the other hand, PBOCST 1 was not patternable until receiving 120° C. PEB, which gave a sensitivity of 17.3 μC/cm$^2$. Further increase of baking temperature to 140° C. improved the sensitivity to 7.8 μC/cm$^2$.

TABLE 1

Sensitivity values of the resist containing PBOCST 1/PHOST 2, HMMM crosslinker, and triphenylsulfonium hexafluoroantimonate photoacid generator. The post-exposure bake duration was 1 minute.

|  | No PEB | 90° C. PEB | 120° C. PEB | 130° C. PEB | 140° C. PEB |
| --- | --- | --- | --- | --- | --- |
| PHOST1 | No Pattern | 51.6 | 7.5 | 6.5 | — |
| PBOCST1 | No Pattern | No Pattern | 17.3 | 12.8 | 7.8 |

(μC/cm$^2$).

Due to the fact that the hydroxyl site, which is required for the crosslinking reaction, is blocked by the acid-labile tBOC protecting group in PBOCST formula, a two-step reaction scheme upon exposure is proposed: the PBOCST is deprotected catalytically to create PHOST, then the hydroxyl group in PHOST reacts with the crosslinkers (Scheme 1). As an approximate 100° C. PEB temperature is required for the effective deprotection of PBOCST in the presence of acid, the data in Table 1 can be well-explained using the two-step proposed mechanism. For the samples without PEB or with 90° C. PEB, insufficient deprotection occurs, thus insufficient amount of OH groups provided for the subsequent crosslinking, resulting in a low sensitivity. The increase of baking temperature promoted the deprotection of PBOCST, driving the sensitivity of PBOCST closer to the PHOST resist. However, the sensitivity of PBOCST did not reach the same value of PHOST at any tested temperatures, which is hypothesized to be a result of reduced catalytic chain length in the two-step reaction.

Resolution Evaluation

With a 30 keV electron beam, fine features were patterned to evaluate the resolution and acid diffusion in the resists. The PEB condition was 130° C./1 min. Rectangles of 2 μm width were patterned with a dose matrix from 10 μC/cm$^2$ to 320 μC/cm$^2$. Although considerable diffusion was observed in both materials, the PBOCST 1 resist (FIG. 1b) had much better CD control compared with the PHOST 1 resist (FIG. 1a). Note that FIG. 1(a) shows only 5 lines (A) obtainable with the resist and a merging of the images (B) at higher exposures, while in FIG. 1(b) 10 lines (C) were obtainable. The capability of better diffusion control of PBOCST 1 might be due to the shortened catalytic chain length resulting from the two-trigger reaction, which suppresses the undesired crosslinking at the pattern edges where acid level is low, whilst having less effect in areas with excess acid. As a result, the chemical contrast between exposure and unexposed areas is enhanced.

Epoxy Acid Activated Crosslinker
Sensitivity Evaluation

The comparative sensitivity of PBOCST 2 and PHOST 2 was evaluated. It is believed that due to an additional epoxide homopolymerization reaction pathway (i.e. crosslinking between epoxy crosslinker molecules), the dependence of resist sensitivity on PEB temperature was different from the resists with HMMM crosslinker (Table 2). An all PGEF epoxy formulation was also studied as a control. Both the PBOCST 2 and PHOST 2 resists were patterned even without PEB. As the sensitivity increased with the PEB temperature, the PHOST 2 reached 7.4 µC/cm² at 130° C. while PBOCST 2 reached 9.6 µC/cm² at 160° C. (Table 2). Some residual film was observed at the unexposed area of PHOST 2 at 160° C. PEB, possibly due to thermal crosslinking. In contrast, the reference resist with just epoxy and PAG had a higher sensitivity without PEB and was ~6 µC/cm² at all PEB temperatures.

Clearly, the introduction of PBOCST 2 or PHOST 2 into the epoxy-PAG system reduced the resist sensitivity, which may be caused by increased glass transition temperature ($T_g$) and reduced crosslinking density. Due to the complexity of crosslinking reactions in the PHOST 2 epoxy resist system, the exact reaction at various PEB temperatures is difficult to evaluate solely from the lithographic performance. However, PBOCST 2 tends to need a higher PEB temperature to reach similar sensitivity level as PHOST 2, which, theoretically, might also indicate an extra deprotection step needed prior to crosslinking. Unexpectedly, the sensitivity of PHOST 2 at 95° C. PEB was lower than the PBOCST 2.

TABLE 2

Sensitivity values PBOCST 2 and PHOST 2. The PEB duration was 1 minute.

|  | No PEB | 95° C. | 130° C. | 160° C. |
|---|---|---|---|---|
| Epoxy + PAG | 13.4 | 5.9 | 5.5 | 5.7 |
| PHOST 2 | 28.9 | 27.3 | 7.4 | — |
| PBOCST 2 | 29.1 | 21.1 | 17.8 | 9.6 |

(µC/cm²)

Resolution Evaluation

The resolution capability of PBOCST 2 and PHOST 2 resists with epoxy PGEF was evaluated using a 30 keV electron beam. 95° C. PEB was applied. Periodical single-pixel lines were patterned. FIG. 2 shows SEM images and critical dimension (CD) values of 60 nm pitch dense lines of the two materials with various doses. The PBOCST 2 resist has smaller CD and wider exposure latitude compared with the PHOST 2 resist. The smallest feature size in the 60 nm pitch line pattern was 20.4 nm for the PHOST 2 and 15.9 nm for the PBOCST 2, respectively. At high doses the PHOST 2 started showing microbridgings, which made the edge detection and CD measurement difficult. Therefore, the CD values for PHOST 2 at dose 191 pC/cm and 216 pC/cm are not shown. It is worth noticing that, with a higher sensitivity at the tested PEB temperature (Table 2), PBOCST 2 still showed smaller CD compared to the PHOST 2 at same doses.

EUV lithography has been used to further evaluate the resolution of the two resist formulations. 1:1 line-space patterns with pitch sizes of 44 nm and 36 nm have been exposed. FIG. 3 shows the SEM images of 44 nm pitch patterns for PHOST 2 and PBOCST 2 resists. Both the two materials have excellent sensitivity of sub-10 mJ/cm². Unlike in the electron beam exposure, where the two resists have similar sensitivity, the PHOST 2 resist shows higher sensitivity than the PBOCST 2 under EUV exposure. The line quality of PBOCST 2 pattern is significantly better, indicating an improved resolution compared with the PHOST 2.

Defocusing Evaluation

To further evaluate the capability of CD control and exposure latitude of the compositions of the current disclosure, a defocusing test was carried out comparing the control and the current resist, where the CD broadening of the PBOCST 2 and PHOST 2 resists upon defocusing the electron beam during exposure was measured.

Using a 30 keV electron beam, isolated single pixel lines were patterned with various doses. Electron beam defocusing was realized by vertically shifting the focal point from 0 up to 20 µm. The SEM images of line patterns are shown in FIG. 4 and FIG. 5. In general, the CDs of PBOCST 2 were smaller than those of PHOST 2, which again reveals a higher resolution capability. The data were then fitted linearly at each dose and the slope reflects the extent of CD broadening with beam defocus. The data show a smaller broadening of PBOCST 2 especially at low doses. It can be clearly seen that the two-trigger resist allows for improved resolution when the exposure is defocused.

We claim:

1. A multiple trigger negative-working photoresist composition comprising:
   a. At least one polymer, oligomer or monomer, each comprising two or more crosslinkable functionalities, wherein essentially all the functionalities are attached to acid labile protecting groups,
   b. at least one acid activated crosslinker, and
   c. at least one photoacid generator.

2. The photoresist composition of claim 1, wherein at least about 90% of the crosslinkable functionalities are attached to acid labile protecting group.

3. The photoresist composition of claim 1, wherein the acid-labile protecting group is capable of being removed when exposed to a photogenerated acid during a post exposure baking process providing a functionality capable of crosslinking with the crosslinker when the crosslinker is exposed to the photogenerated acid.

4. The photoresist composition of claim 1, wherein the acid labile protecting group comprises a tertiary alkoxycarbonyl group.

5. The photoresist composition of claim 1, wherein the at least one photoacid generator comprises an onium salt compound, a triphenylsulphonium salt, a sulfonimide, a halogen-containing compound, a sulfone, a sulfonate ester, a quinone-diazide, a diazomethane, an iodonium salt, an oxime sulfonate, or a dicarboxyimidyl sulfate.

6. The photoresist composition of claim 1, wherein the at least one acid activated crosslinker comprises a monomer, oligomer or polymer.

7. The photoresist composition of claim 1, wherein the at least one acid activated crosslinker comprises at least one of a glycidyl ether, glycidyl ester, an oxetane, a glycidyl amine, a methoxymethyl group, an ethoxy methyl group, a butoxymethyl group, a benzyloxymethyl group, dimethylamino methyl group, diethylamino methyl amino group, a dialkylolmethyl amino group, a dibutoxymethyl amino group, a dimethylolmethyl amino group, diethylolmethyl amino group, a dibutylolmethyl amino group, a morpholinomethyl group, acetoxymethyl group, benzyloxymethyl group, formyl group, acetyl group, vinylgroup or an isopropenyl group.

8. The photoresist composition of claim 1, wherein the at least one acid activated crosslinker comprises one or more glycidyl ether groups attached to an aryl monomer, oligomer or polymer.

9. The photoresist composition of claim 1, which is photoimageable by at least one of UV, deep UV, extreme UV, x-ray, or e-beam actinic radiation.

10. The photoresist composition of claim 1, wherein the photoresist is capable of being developed in solvent, aqueous base or combinations thereof.

11. A method of forming a patterned resist layer on a substrate comprising the steps of:
   a. providing a substrate,
   b. applying the multiple trigger negative working photoresist composition of claim 1 to a desired wet thickness,
   c. heating the coated substrate to form a substantially dried coating to obtain a desired thickness,
   d. imagewise exposing the coated substrate to actinic radiation, and
   e. removing the unexposed areas of the coating using an aqueous, solvent or a combination aqueous-solvent developer composition;
      wherein the remaining photoimage pattern is optionally heated.

12. The method of claim 11, wherein the actinic radiation is chosen from one or more of UV, deep UV, extreme UV, x-ray, or e-beam actinic radiation.

13. The method of claim 11, wherein at least about 90% of the crosslinkable functionalities are attached to acid labile protecting group.

14. The method of claim 11, wherein the acid labile protecting group is capable of being removed when exposed to acid under ambient conditions providing a functionality capable of crosslinking with the crosslinking system when the crosslinking system is catalyzed by acid.

15. The method of claim 11, wherein the acid labile protecting group comprises a tertiary alkoxycarbonyl group.

16. The method of claim 11, wherein the at least one photoacid generator comprises an onium salt compound, a triphenylsulphonium salt, a sulfonimide, a halogen-containing compound, a sulfone, a sulfonate ester, a quinonediazide, a diazomethane, an iodonium salt, an oxime sulfonate, or a dicarboxyimidyl sulfate.

17. The method of claim 11, wherein the at least one acid activated crosslinker comprises a monomer, oligomer or polymer.

18. The method of claim 11, wherein the at least one acid activated crosslinker comprises at least one of a glycidyl ether, glycidyl ester, glycidyl amine, a methoxymethyl group, an ethoxy methyl group, a butoxymethyl group, a henzyloxymethyl group, dimethylamino methyl group, diethylamino methyl amino group, a dialkylolmethyl amino group, a dibutoxymethyl amino group, a dimethylolmethyl amino group, diethylolmethyl amino group, a dibutylol methyl amino group, a morpholino methyl group, acetoxymethyl group, benzyloxy methyl group, formyl group, acetyl group, vinylgroup, an isopropenyl group, or one or more glycidyl ether groups attached to an aryl monomer, oligomer or polymer.

* * * * *